United States Patent
Takemoto

(10) Patent No.: US 10,314,663 B2
(45) Date of Patent: Jun. 11, 2019

(54) MEDICAL OVERTUBE

(71) Applicant: OLYMPUS CORPORATION, Tokyo (JP)

(72) Inventor: Shotaro Takemoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/824,481

(22) Filed: Nov. 28, 2017

(65) Prior Publication Data
US 2018/0078282 A1  Mar. 22, 2018

Related U.S. Application Data

(63) Continuation of application No. PCT/JP2016/063786, filed on May 9, 2016.
(Continued)

(51) Int. Cl.
*A61B 17/34* (2006.01)
*A61B 46/10* (2016.01)
(Continued)

(52) U.S. Cl.
CPC ........ *A61B 46/10* (2016.02); *A61B 17/00234* (2013.01); *A61B 17/29* (2013.01); *A61B 17/3423* (2013.01); *A61B 34/30* (2016.02); *A61B 34/32* (2016.02); *A61B 34/37* (2016.02); *A61B 34/70* (2016.02); *A61B 34/71* (2016.02); *A61B 34/74* (2016.02); *A61B 90/03* (2016.02);
(Continued)

(58) Field of Classification Search
CPC ........ A61B 17/0218; A61B 2017/0225; A61B 17/3421; A61B 2017/3433; A61B 2017/3445; A61B 2017/3447; A61B 2017/3449

USPC .................................................. 600/201–246
See application file for complete search history.

(56) References Cited

U.S. PATENT DOCUMENTS 5,386,816 A   2/1995   Inoue et al.
5,681,322 A   10/1997  Hartigan, Jr.
(Continued)

FOREIGN PATENT DOCUMENTS

CN   101416867 A   4/2009
EP   2324789 A1    5/2011
(Continued)

OTHER PUBLICATIONS

Office Action dated Jan. 30, 2018 received in U.S. Appl. No. 15/375,374.
(Continued)

*Primary Examiner* — Julianna N Harvey
*Assistant Examiner* — Christina Negrellirodriguez
(74) *Attorney, Agent, or Firm* — Scully, Scott, Murphy & Presser, P.C.

(57) ABSTRACT

A medical overtube includes a multi-lumen tube provided with a plurality of lumens through which medical devices are to be passed; a braided tube which covers an outer side of the multi-lumen tube and is made of braided fibers; and an outer tube that covers an outer side of the braided tube, wherein a through hole is formed in the multi-lumen tube or the outer tube, the through hole is configured to connect a space, which is covered by the outer tube and the multi-lumen tube and in which the braided tube is disposed, to an exterior.

5 Claims, 7 Drawing Sheets

Related U.S. Application Data

(60) Provisional application No. 62/168,987, filed on Jun. 1, 2015.

(51) Int. Cl.
| | |
|---|---|
| *A61B 34/32* | (2016.01) |
| *A61B 34/37* | (2016.01) |
| *A61B 34/00* | (2016.01) |
| *A61B 90/00* | (2016.01) |
| *A61B 17/29* | (2006.01) |
| *B25J 3/00* | (2006.01) |
| *B25J 13/02* | (2006.01) |
| *A61B 90/50* | (2016.01) |
| *A61B 17/00* | (2006.01) |
| *A61B 34/30* | (2016.01) |
| *A61M 25/00* | (2006.01) |
| *A61L 2/20* | (2006.01) |
| *A61B 18/14* | (2006.01) |
| *B32B 3/26* | (2006.01) |
| *A61B 18/00* | (2006.01) |
| *A61M 39/08* | (2006.01) |

(52) U.S. Cl.
CPC .............. *A61B 90/06* (2016.02); *A61B 90/50* (2016.02); *A61L 2/206* (2013.01); *A61M 25/005* (2013.01); *A61M 25/0012* (2013.01); *A61M 25/0015* (2013.01); *B25J 3/00* (2013.01); *B25J 13/02* (2013.01); *A61B 18/1482* (2013.01); *A61B 18/1492* (2013.01); *A61B 2017/00314* (2013.01); *A61B 2017/00323* (2013.01); *A61B 2017/00477* (2013.01); *A61B 2017/00929* (2013.01); *A61B 2018/00077* (2013.01); *A61B 2018/00083* (2013.01); *A61B 2018/1412* (2013.01); *A61B 2034/301* (2016.02); *A61B 2034/302* (2016.02); *A61B 2034/306* (2016.02); *A61B 2090/034* (2016.02); *A61B 2217/005* (2013.01); *A61B 2218/007* (2013.01); *A61M 2025/0004* (2013.01); *A61M 2025/0019* (2013.01); *A61M 2039/082* (2013.01); *B32B 3/266* (2013.01); *H05K 999/99* (2013.01)

(56) References Cited

U.S. PATENT DOCUMENTS

| | | | |
|---|---|---|---|
| 6,331,181 | B1 | 12/2001 | Tierney et al. |
| 7,972,298 | B2 | 7/2011 | Wallace et al. |
| 8,638,057 | B2 | 1/2014 | Goldberg et al. |
| 8,720,448 | B2 | 5/2014 | Reis et al. |
| 2002/0128649 | A1 | 9/2002 | Bacher et al. |
| 2004/0019352 | A1 | 1/2004 | Kidooka |
| 2005/0075739 | A1 | 4/2005 | Nishizawa |
| 2005/0096502 | A1 | 5/2005 | Khalili |
| 2005/0154439 | A1 | 7/2005 | Gunderson |
| 2005/0222495 | A1 | 10/2005 | Okada et al. |
| 2005/0272975 | A1 | 12/2005 | McWeeney et al. |
| 2006/0282063 | A1 | 12/2006 | Gotani |
| 2007/0163597 | A1 | 7/2007 | Mikkaichi et al. |
| 2008/0108443 | A1 | 5/2008 | Jinno et al. |
| 2008/0193260 | A1 | 8/2008 | Yokokohji et al. |
| 2008/0281155 | A1 | 11/2008 | Fujikura |
| 2008/0294004 | A1 | 11/2008 | Fujikura |
| 2009/0018390 | A1 | 1/2009 | Honda et al. |
| 2009/0105726 | A1 | 4/2009 | Sugiyama |
| 2009/0182200 | A1* | 7/2009 | Golden ............ A61M 25/0043 600/153 |
| 2009/0248039 | A1 | 10/2009 | Cooper et al. |
| 2009/0275798 | A1 | 11/2009 | Naito |
| 2010/0030023 | A1 | 2/2010 | Yoshie |
| 2010/0170519 | A1 | 7/2010 | Romo et al. |
| 2010/0298646 | A1* | 11/2010 | Stellon ............... A61B 17/3423 600/208 |
| 2010/0318100 | A1 | 12/2010 | Okamoto et al. |
| 2010/0331856 | A1 | 12/2010 | Carlson et al. |
| 2011/0168189 | A1 | 7/2011 | Cooper et al. |
| 2012/0271102 | A1 | 10/2012 | Katayama |
| 2012/0289973 | A1 | 11/2012 | Prisco et al. |
| 2013/0331857 | A9 | 12/2013 | Prisco et al. |
| 2014/0166023 | A1 | 6/2014 | Kishi |
| 2014/0188089 | A1 | 7/2014 | Midgette et al. |
| 2014/0296771 | A1 | 10/2014 | Naito |
| 2015/0025507 | A1 | 1/2015 | Golden et al. |
| 2015/0238180 | A1* | 8/2015 | Weitzner ............. A61B 1/0014 600/208 |
| 2017/0361064 | A1 | 12/2017 | Golden et al. |

FOREIGN PATENT DOCUMENTS

| | | |
|---|---|---|
| EP | 2 891 449 A1 | 7/2015 |
| JP | S6272091 U | 5/1987 |
| JP | H05095893 A | 4/1993 |
| JP | H07095953 A | 4/1995 |
| JP | H10276965 A | 10/1998 |
| JP | 2004344180 A | 12/2004 |
| JP | 2005103741 A | 4/2005 |
| JP | 2005287963 A | 10/2005 |
| JP | 2006334695 A | 12/2006 |
| JP | 2007167644 A | 7/2007 |
| JP | 2007517597 A | 7/2007 |
| JP | 2007307289 A | 11/2007 |
| JP | 2007530155 A | 11/2007 |
| JP | 2008114339 A | 5/2008 |
| JP | 2008278968 A | 11/2008 |
| JP | 2009011809 A | 1/2009 |
| JP | 2009100873 A | 5/2009 |
| JP | 2009523032 A | 6/2009 |
| JP | 2009240657 A | 10/2009 |
| JP | 2009268592 A | 11/2009 |
| JP | 4420593 B2 | 2/2010 |
| JP | 2010035768 A | 2/2010 |
| JP | 2010525838 A | 7/2010 |
| JP | 2011509718 A | 3/2011 |
| JP | 2011072570 A | 4/2011 |
| JP | 2011072574 A | 4/2011 |
| JP | 2012070953 A | 4/2012 |
| JP | 2012152562 A | 8/2012 |
| JP | 2013034833 A | 2/2013 |
| JP | 2014028291 A | 2/2014 |
| JP | 2014111080 A | 6/2014 |
| JP | 2014521375 A | 8/2014 |
| JP | 2015006423 A | 1/2015 |
| JP | 2018-108430 A | 7/2018 |
| WO | 1997029690 A1 | 8/1997 |
| WO | 1998025666 A1 | 6/1998 |
| WO | 2005070339 A1 | 8/2005 |
| WO | 2005094665 A2 | 10/2005 |
| WO | 2007041093 A1 | 4/2007 |
| WO | 2007070693 A2 | 6/2007 |
| WO | 2009037576 A2 | 3/2009 |
| WO | 2009091836 A1 | 7/2009 |
| WO | 2010055745 A1 | 5/2010 |
| WO | 2012158449 A1 | 11/2012 |
| WO | 2013018927 A1 | 2/2013 |
| WO | 2014034532 A1 | 3/2014 |
| WO | 2014106047 A1 | 7/2014 |

OTHER PUBLICATIONS

International Search Report dated Jun. 28, 2016 issued in International Application No. PCT/JP2016/063786.
U.S. Office Action dated Sep. 14, 2017 issued in U.S. Appl. No. 15/375,374.
International Search Report dated Nov. 10, 2015 issued in International Application No. PCT/JP2015/074792.
International Search Report dated Jan. 26, 2016 issued in International Application No. PCT/JP2015/082622.
International Search Report dated Jan. 12, 2016 issued in International Application No. PCT/JP2015/082118.

(56) References Cited

OTHER PUBLICATIONS

International Search Report dated Dec. 22, 2015 issued in International Application No. PCT/JP2015/078063.
Office Action dated Apr. 19, 2018 received in U.S. Appl. No. 15/804,068.
Office Action dated Apr. 19, 2018 received in U.S. Appl. No. 15/819,045.
Extended Supplementary European Search Report dated Dec. 19, 2018 in European Patent Application No. 16 80 2987.4.

* cited by examiner

MEDICAL OVERTUBE

CROSS-REFERENCE TO RELATED APPLICATIONS

This application is a Continuation Application of International Application No. PCT/JP2016/063786 filed on May 9, 2016, which claims priority to Provisional Application No. 62/168,987 filed on Jun. 1, 2015. The Contents of International Application No. PCT/JP2016/063786 and Provisional application No. 62/168,987 are hereby incorporated herein by reference in their entirety.

TECHNICAL FIELD

The present invention relates to a medical overtube.

BACKGROUND ART

A three-layer-structure medical overtube that includes an elongated multi-lumen tube having a plurality of through holes through which medical devices are to be passed, a braided tube that covers an outer side of the multi-lumen tube and is composed of braided fibers, and an outer tube that covers an outer side of the braided tube is well known (for example, refer to PTL 1).

CITATION LIST

Patent Literature

{PTL 1} Japanese Translation of PCT International Application, Publication No. 2011-509718

SUMMARY OF INVENTION

An aspect of the present invention provides a medical overtube that includes a multi-lumen tube provided with a plurality of lumens through which medical devices are to be passed; a braided tube which covers an outer side of the multi-lumen tube and which is made of braided fibers; and an outer tube that covers an outer side of the braided tube, wherein a through hole is formed in the multi-lumen tube or the outer tube, the through hole is configured to connect a space, which is covered by the outer tube and the multi-lumen tube and in which the braided tube is disposed, to an exterior.

DESCRIPTION OF EMBODIMENT

A medical overtube 1 according to an embodiment of the present invention will now be described with reference to the drawings.

Figure 1:
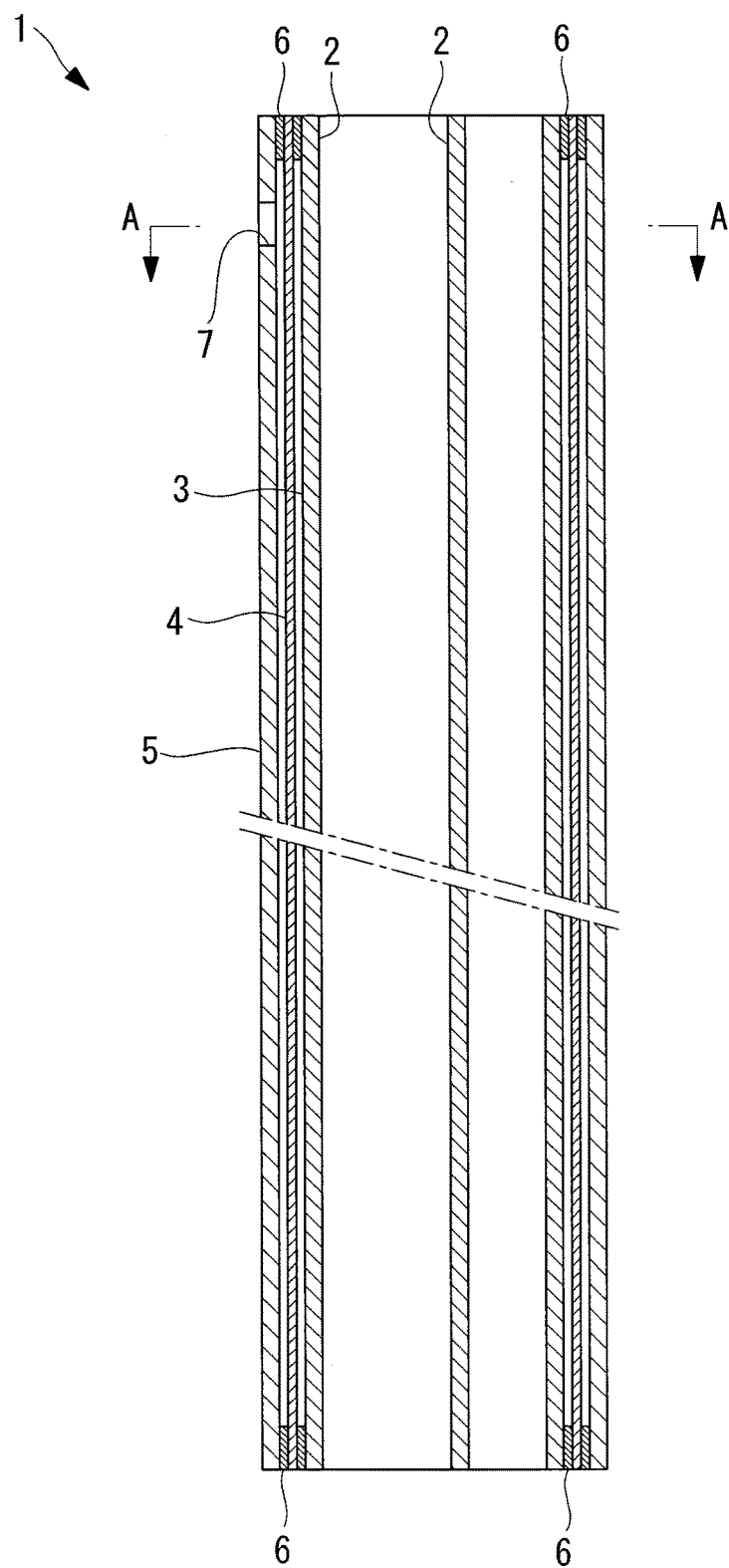
FIG. 1 is a longitudinal sectional view which shows a medical overtube according to a first embodiment of the present invention and which is taken along B-B in FIG. 2.
Figure 2:
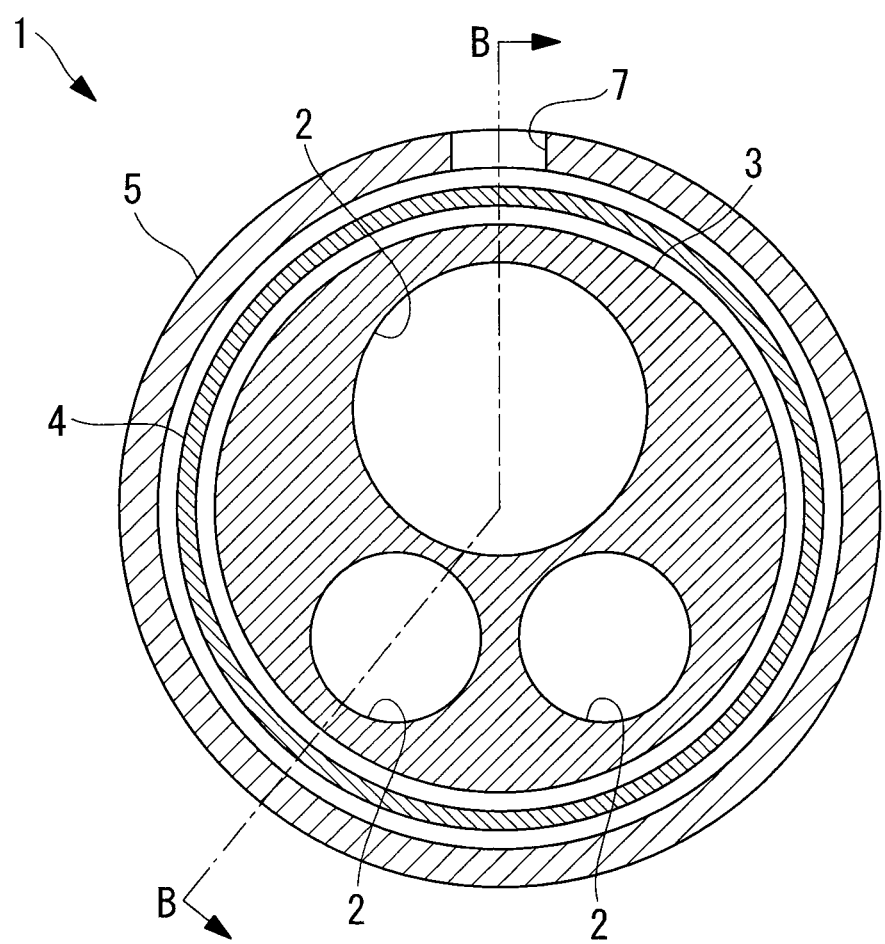
FIG. 2 is a lateral sectional view which shows the medical overtube illustrated in FIG. 1 and which is taken along A-A in FIG. 1 at the position of a through hole.

As illustrated in FIGS. 1 and 2, the medical overtube 1 according to this embodiment has a multi-lumen tube 3 which has a plurality of lumens 2 penetrating in the longitudinal direction and which is composed of a flexible material, a braided tube 4 composed of braided fibers and disposed so as to cover the outer side of the multi-lumen tube 3 around the entirety thereof, and an outer tube 5 disposed so as to cover the outer side of the braided tube 4 around the entirety thereof.

The lumens 2 of the multi-lumen tube 3 are configured to allow insertion of medical devices, such as an endoscope, an optical fiber, a treatment tool, and the like. The multi-lumen tube 3 is composed of a highly airtight resin material.

The braided tube 4 is a tube formed by braiding resin fibers or metal fibers, and can transmit torsional torque about the longitudinal axis.

The outer tube 5 is a highly airtight resin tube with a smooth surface and has a small wall thickness. Because the outer surface of the braided tube 4 is covered with the outer tube 5, friction occurring during insertion into the body is reduced, and the insertability is improved.

The space between the multi-lumen tube 3 and the braided tube 4 and the space between the braided tube 4 and the outer tube 5 are put in a hermetically sealed state by bonding them by an adhesive 6 at the two ends in the longitudinal direction of the medical overtube 1.

The medical overtube 1 according to this embodiment is equipped with a through hole 7, which is located near the proximal end of the outer tube 5 and penetrates through the outer tube 5 in the radial direction. The through hole 7 causes a cylindrical space, which is formed between the outer surface of the multi-lumen tube 3 and the inner surface of the outer tube 5 and in which the braided tube 4 is disposed, to be open to the atmosphere in a radially outward direction.

The functions of the medical overtube 1 according to this embodiment having the above-described structure will now be described.

When the medical overtube 1 according to this embodiment is being inserted into a body cavity of a patient, the multi-lumen tube 3, the braided tube 4, and the outer tube 5 bend to follow the shape of the body cavity. Since the outer tube 5 has a smooth surface, friction that occurs during insertion is reduced, and the medical overtube 1 can be smoothly inserted.

Medical devices, such as an endoscope and a treatment tool, are inserted into the plurality of lumens 2 of the multi-lumen tube 3 so that the affected area can be treated with the treatment tool while being observed with the endoscope.

In order to rotate the field of view of the endoscope during treatment of the affected area, torsional torque about the longitudinal axis is applied to the proximal end of the medical overtube 1. Since the medical overtube 1 according to this embodiment is equipped with the braided tube 4 that can transmit the torsional torque, the torsional torque applied to the proximal end can be transmitted to the distal end, and the medical devices protruding from the distal end openings of the lumens 2 can be simultaneously rotated without changing the relative position thereof.

In order to sterilize the medical overtube 1 according to this embodiment, the medical overtube 1 is placed in a hermetically sealable processing chamber, and the inside of the processing chamber is vacuum-suctioned to evacuate air. Since the braided tube 4 is composed of braided fibers, air is contained therein. Moreover, the space in which the braided tube 4 is disposed is sealed at the distal end portion and the proximal end portion by using the adhesive 6.

In this embodiment, because the through hole 7 that penetrates the outer tube 5 in the radial direction is provided, the air inside the space in which the braided tube 4 is disposed is evacuated through the through hole 7 by vacuum suction. As a result, the space in which the braided tube 4 is disposed is prevented from expanding even when the pressure is decreased by vacuum suction, and rupturing of the outer tube 5 can be reliably prevented. Moreover, since the through hole 7 is provided on the proximal end side of the outer tube 5, the through hole 7 stays out of the body cavity, and entry of body fluids into the space in which the braided tube 4 is disposed can be prevented.

When ethylene oxide gas is supplied to the processing chamber in such a state, the medical overtube 1 can be sterilized with highly concentrated ethylene oxide gas. The highly concentrated ethylene oxide gas supplied also reaches, through the through hole 7, the space in which the braided tube 4 is disposed. As a result, the space in which the braided tube 4 is disposed can also be sterilized.

Figure 3:
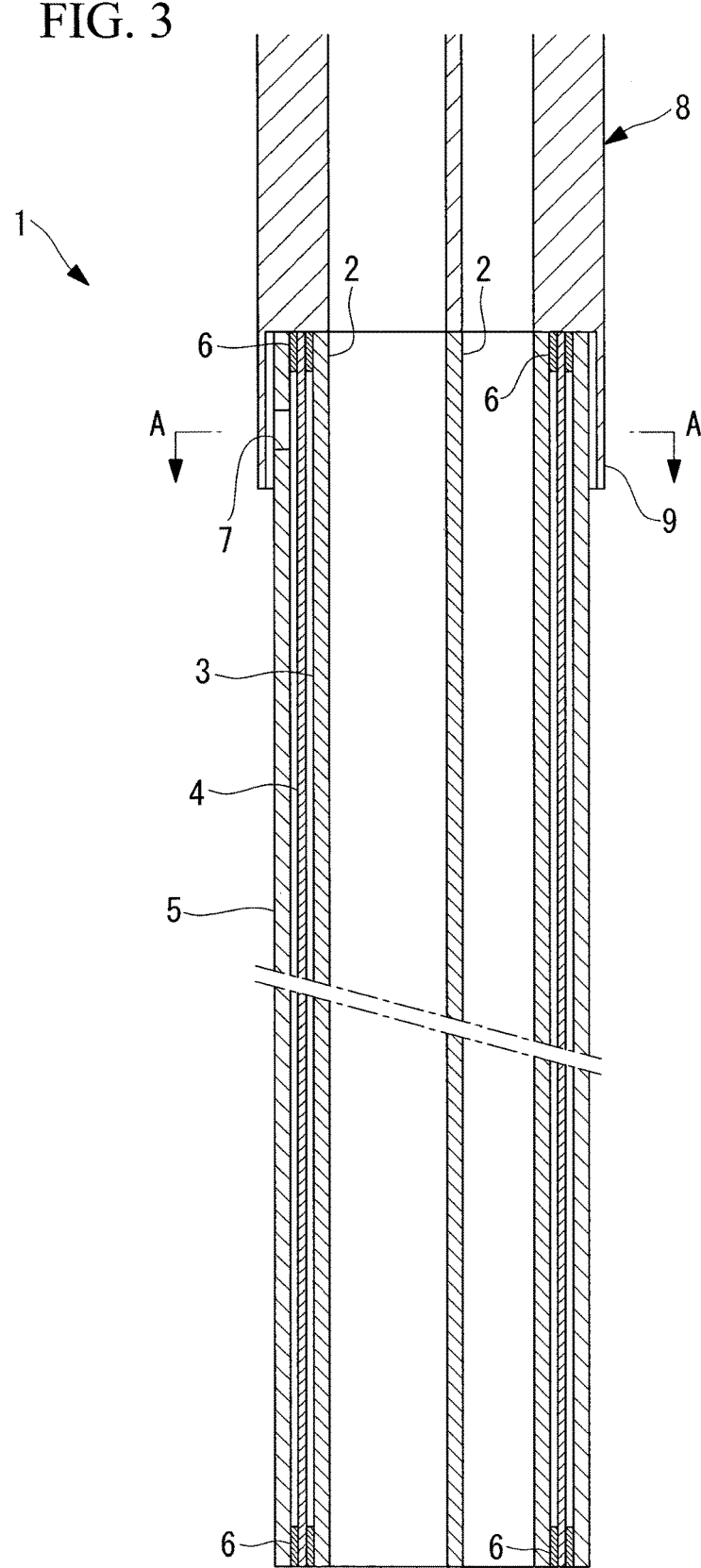
FIG. 3 is a longitudinal sectional view which shows a first modification of the medical overtube illustrated in FIG. 1 and which is taken along B-B in FIG. 4.
Figure 4:
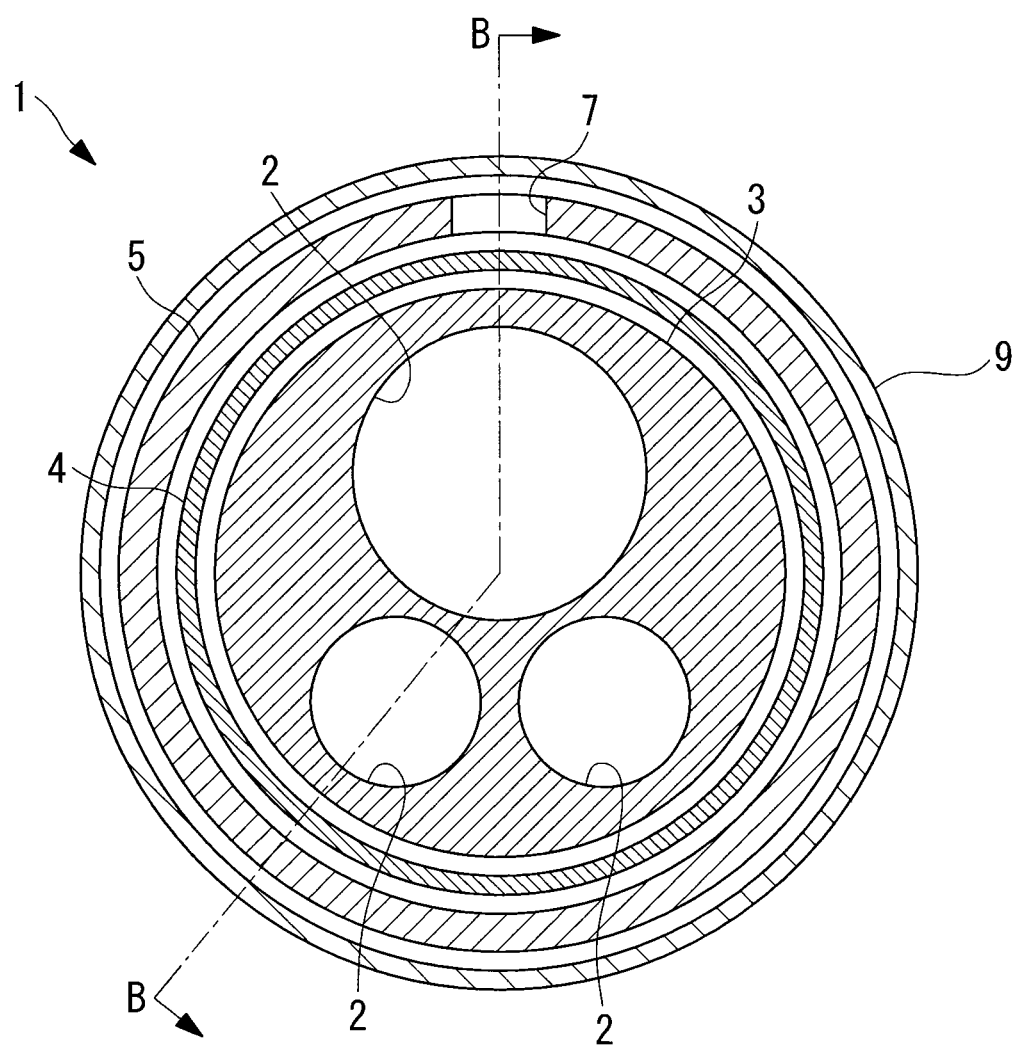
FIG. 4 is a lateral sectional view which shows the medical overtube illustrated in FIG. 3 and which is taken along A-A in FIG. 3 at the position of a through hole.

As illustrated in FIGS. 3 and 4, in this embodiment, a cylindrical cover portion 9 that extends from an operation unit 8, which is attached to the proximal end of the medical overtube 1, toward the distal end up to a position at which the cylindrical cover portion 9 covers the opening (opening portion) of the through hole 7 may be provided. The cover portion 9 is disposed so as to leave a space in the radial direction with respect to the outer surface of the outer tube 5.

In this manner, when the medical overtube 1 is being sterilized in a sterilizing pack, the opening of the through hole 7 in the outer tube 5 can be prevented from becoming closed by the film that constitutes the sterilizing pack. In other words, although the film is disposed to cover the cover portion 9, the space formed between the cover portion 9 and the outer tube 5 allows the air to be evacuated therethrough, and ethylene oxide gas can be supplied to the space in which the braided tube 4 is disposed.

Figure 5:
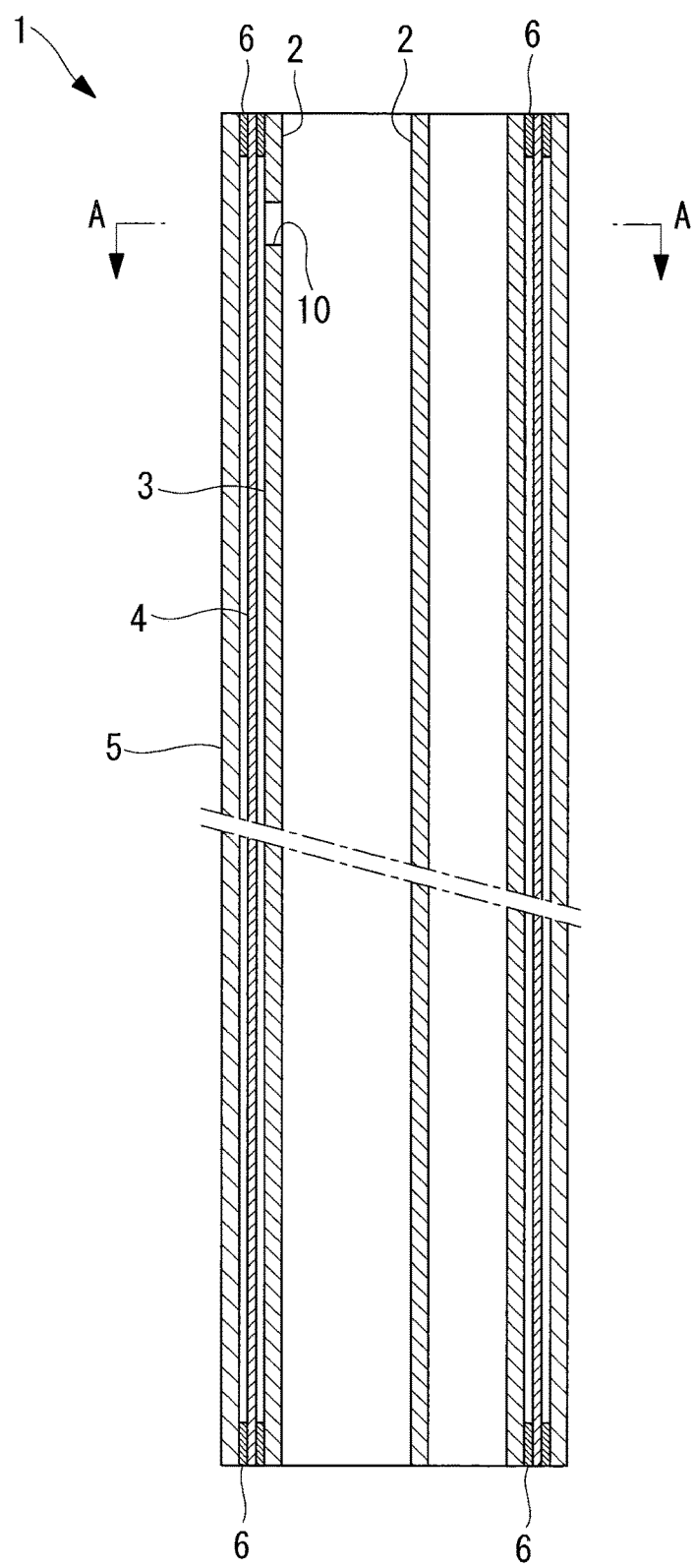
FIG. 5 is a longitudinal sectional view which shows a second modification of the medical overtube illustrated in FIG. 1 and which is taken along B-B in FIG. 6.
Figure 6:
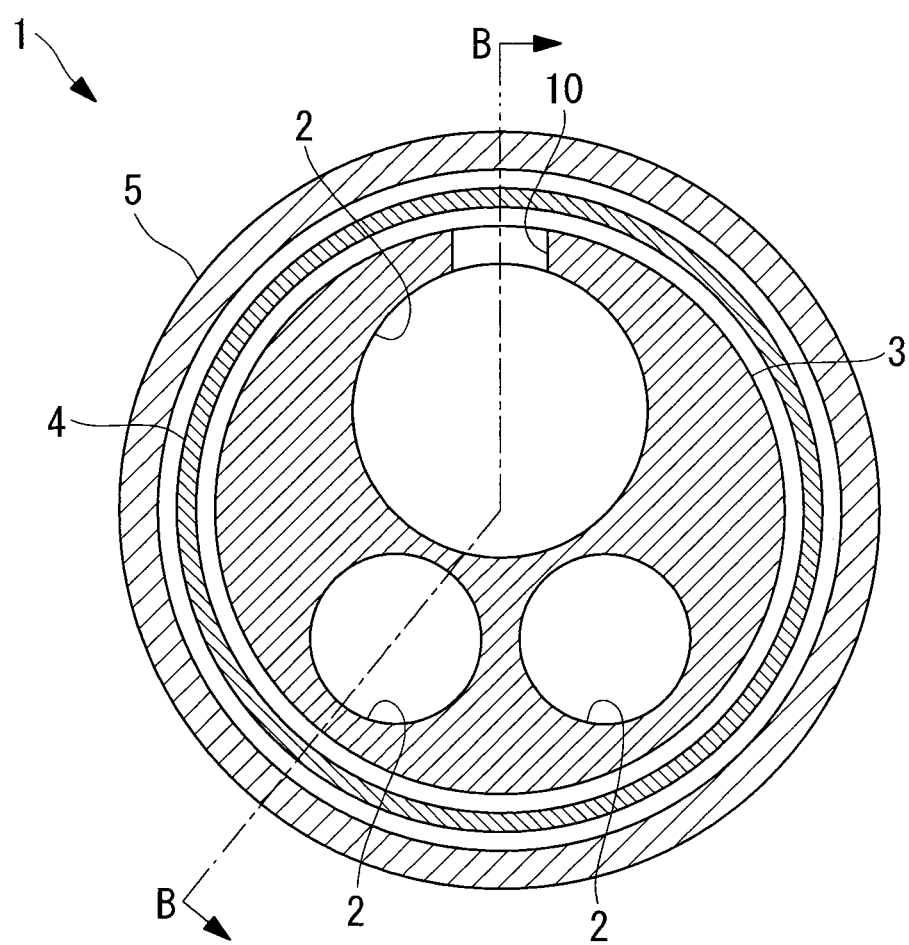
FIG. 6 is a lateral sectional view which shows the medical overtube illustrated in FIG. 5 and which is taken along A-A in FIG. 5 at the position of a through hole.

In this embodiment, the through hole 7 is formed in the outer tube 5, In another embodiment, as illustrated in FIGS. 5 and 6, a through hole 10 that allows the outer surface of the multi-lumen tube 3 and one of the lumens 2 to be in communication with each other may be formed. Since the opening of the through hole 10 is disposed inside the lumen 2, there are advantages in that the opening of the through hole 10 is prevented from becoming closed by the film of the sterilizing pack, and sterilization can be reliably carried out.

Figure 7:
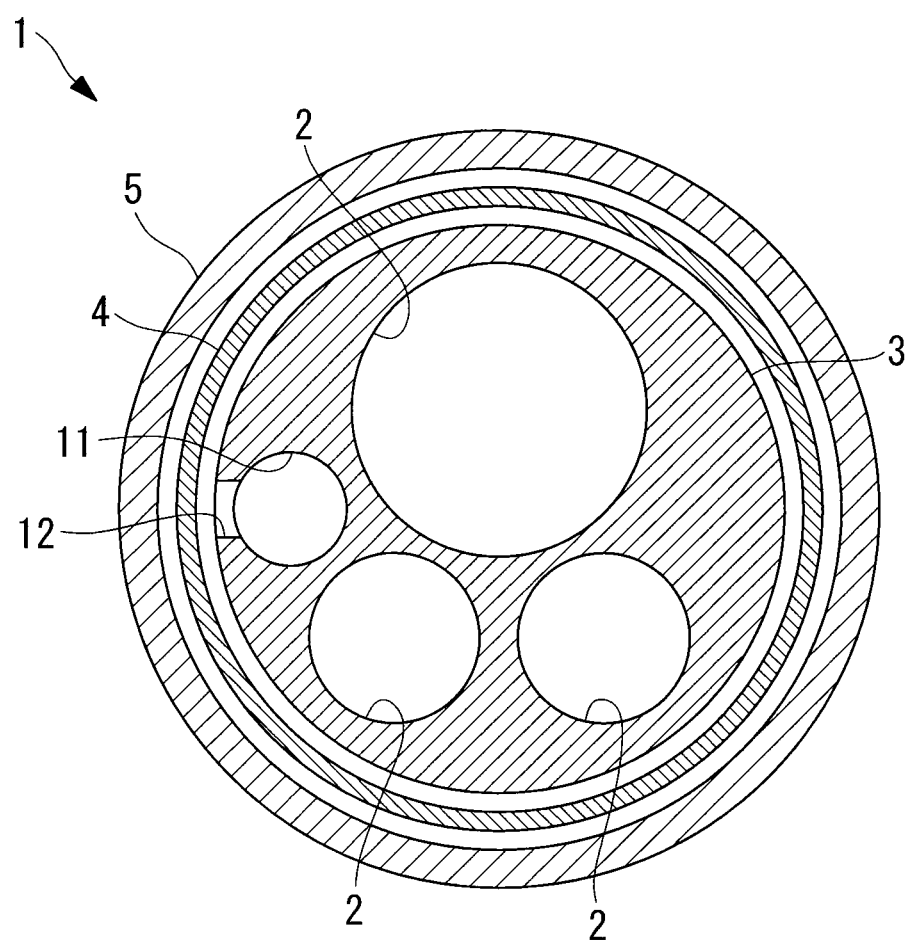
FIG. 7 is a lateral sectional view which shows a third modification of the medical overtube illustrated in FIG. 1 and which is taken at the position of a through hole.

As illustrated in FIG. 7, instead of providing the through hole 10 in one of the lumens 2 through which medical devices are passed, a through hole 12 may be provided in a dedicated evacuation lumen 11. The evacuation lumen 11 may be any lumen as long as the distal end opening at the distal end of the medical overtube 1 is closed and the proximal end opening at the proximal end of the medical overtube 1 is open to the atmosphere.

In this manner, body fluids are prevented from entering the evacuation lumen 11, and thus entry of body fluids into the space in which the braided tube 4 is disposed can be prevented.

The inventor has arrived at the following aspects of the present invention.

An aspect of the present invention provides a medical overtube that includes a multi-lumen tube provided with a plurality of lumens through which medical devices are to be passed; a braided tube which covers an outer side of the multi-lumen tube and which is made of braided fibers; and an outer tube that covers an outer side of the braided tube, wherein a through hole is formed in the multi-lumen tube or the outer tube, the through hole is configured to connect a space, which is covered by the outer tube and the multi-lumen tube and in which the braided tube is disposed, to an exterior.

According to this aspect, torsional torque applied to a proximal end of the medical overtube can be transmitted to a distal end of the medical overtube by the braided tube disposed between the multi-lumen tube and the outer tube, and the medical devices that have been passed through the lumens of the multi-lumen tube can be rotated simultaneously while keeping the relative position.

In order to sterilize the medical overtube in this case, the medical overtube is placed in the processing chamber, vacuum suction is carried out to evacuate air inside the processing chamber, and then the inside of the processing chamber is filled with ethylene oxide gas so as to conduct a sterilization process with highly concentrated ethylene oxide gas. During vacuum suction, the pressure inside the processing chamber is reduced. However, because the space, which lies between the outer tube and the multi-lumen tube and in which the braided tube is disposed, is connected to the exterior through the through hole formed in the multi-lumen tube or the outer tube, the air inside this space is evacuated to the exterior through the through hole, and thereby expansion and rupture of the outer tube can be prevented.

In the aspect described above, the through hole may be provided to penetrate through the outer tube in a radial direction.

In the aspect described above, a cover portion that covers an opening of the through hole may be provided at a radially outer side of the outer tube so that a space between the opening and the cover portion is made in the radial direction.

In this manner, even when the pressure is reduced by vacuum suction performed prior to the sterilization process, because the space that lies between the outer tube and the multi-lumen tube and in which the braided tube is disposed is connected to the exterior through the through hole formed in the outer tube, the air inside the space is evacuated to the exterior through the through hole, and expansion and rupture of the outer tube can be prevented.

Under this condition, even when the medical overtube is sterilized in a sterilizing pack, the cover portion prevents closure of the through hole by the film that constitutes the sterilizing pack. Thus, air inside the space in which the braided tube is disposed can be more reliably evacuated to the exterior.

Alternatively, in the aspect described above, the through hole may be provided to penetrate from an outer surface of the multi-lumen tube to one of the lumens.

In this manner, even when the medical overtube is sterilized in a sterilizing pack, air inside the space in which the braided tube is disposed is evacuated to the exterior through the through hole that penetrates one of the lumens. Since the through hole does not have an opening in the outer surface of the outer tube, closure of the through hole by the film that constitutes the sterilizing pack can be prevented.

In the aspect described above, the multi-lumen tube may be provided with an evacuation lumen having a closed distal end opening and an open proximal end opening, and the through hole can be provided so as to penetrate from the outer surface of the multi-lumen tube to the evacuation lumen.

In this manner, even when the medical overtube is inserted into the body, the evacuation lumen, which has a closed distal end opening, is prevented from becoming contaminated with body fluids. Moreover, since no medical devices are to be passed through the evacuation lumen, contamination inside the lumen caused by insertion and withdrawal of the medical devices can be prevented as well. Thus, entry of substances, such as body fluids, into the space in which the braided tube is disposed can be prevented.

An advantageous effect offered by the aforementioned aspects is that the medical overtube remains undamaged and can maintain in a good shape despite vacuum suction in an EOG sterilization process.

REFERENCE SIGNS LIST 1 medical overtube
2 lumen
3 multi-lumen tube
4 braided tube
5 outer tube
7, 10, 12 through hole
9 cover portion
11 evacuation lumen

The invention claimed is:

1. A medical overtube comprising:
a multi-lumen tube provided with a plurality of lumens through which medical devices are to be passed;
a braided tube which covers an outer side of the multi-lumen tube and which is made of braided fibers; and
an outer tube that covers an outer side of the braided tube,
wherein a through hole is formed in the outer tube, the through hole is configured to connect a space, which is covered by the outer tube and the multi-lumen tube and in which the braided tube is disposed, to an exterior, wherein the through hole is provided to penetrate through the outer tube in a radial direction.

2. The medical overtube according to claim 1, wherein a cover portion that covers an opening of the through hole is provided at a radially outer side of the outer tube so that a space between the opening and the cover portion is made in the radial direction.

3. A medical overtube comprising:
a multi-lumen tube provided with a plurality of lumens through which medical devices are to be passed;
a braided tube which covers an outer side of the multi-lumen tube and which is made of braided fibers; and
an outer tube that covers an outer side of the braided tube,
wherein a through hole is formed in the multi-lumen tube, the through hole is configured to connect a space, which is covered by the outer tube and the multi-lumen tube and in which the braided tube is disposed, to an exterior,
wherein the through hole is provided to penetrate from an outer surface of the multi-lumen tube to one of the lumens,
wherein the multi-lumen tube is provided with an evacuation lumen having a closed distal end opening and an open proximal end opening, and
the through hole is provided so as to penetrate from the outer surface of the multi-lumen tube to the evacuation lumen.

4. The medical overtube according to claim 3, wherein the through hole is provided to penetrate from an outer surface of the multi-lumen tube to one of the lumens.

5. The medical overtube according to claim 4, wherein the multi-lumen tube is provided with an evacuation lumen having a closed distal end opening and an open proximal end opening, and
the through hole is provided so as to penetrate from the outer surface of the multi-lumen tube to the evacuation lumen.

* * * * *